(12) United States Patent
Kitamura et al.

(10) Patent No.: US 12,329,504 B2
(45) Date of Patent: Jun. 17, 2025

(54) VITAL SENSOR

(71) Applicant: MINEBEA MITSUMI Inc., Nagano (JP)

(72) Inventors: Atsushi Kitamura, Nagano (JP); Shigeyuki Adachi, Nagano (JP); Toshiaki Asakawa, Nagano (JP); Yosuke Ogasa, Nagano (JP)

(73) Assignee: MINEBEA MITSUMI Inc., Nagano (JP)

( * ) Notice: Subject to any disclaimer, the term of this patent is extended or adjusted under 35 U.S.C. 154(b) by 0 days.

(21) Appl. No.: 18/562,535

(22) PCT Filed: Mar. 25, 2022

(86) PCT No.: PCT/JP2022/014727
§ 371 (c)(1),
(2) Date: Nov. 20, 2023

(87) PCT Pub. No.: WO2022/249717
PCT Pub. Date: Dec. 1, 2022

(65) Prior Publication Data
US 2024/0268692 A1 Aug. 15, 2024

Related U.S. Application Data

(60) Provisional application No. 63/193,162, filed on May 26, 2021.

(30) Foreign Application Priority Data

Jul. 2, 2021 (JP) .................................. 2021-111065

(51) Int. Cl.
*A61B 5/026* (2006.01)

(52) U.S. Cl.
CPC ..................................... *A61B 5/026* (2013.01)

(58) Field of Classification Search
CPC ....................................................... A61B 5/026
See application file for complete search history.

(56) References Cited

U.S. PATENT DOCUMENTS

2006/0005631 A1  1/2006  Hashimoto et al.
2015/0016487 A1*  1/2015  Britton .................... G01L 1/205
                                                           374/185

(Continued)

FOREIGN PATENT DOCUMENTS

JP  2002-078689  3/2002
JP  2005-021452  1/2005

(Continued)

OTHER PUBLICATIONS

International Search Report for PCT/JP2022/014727 mailed on Jun. 7, 2022.

*Primary Examiner* — Xin Y Zhong
(74) *Attorney, Agent, or Firm* — IPUSA, PLLC

(57) ABSTRACT

The present vital sensor is a vital sensor configured to monitor a blood flow, and includes a strain generator to be attached to a measurement site in a subject, and a strain gauge disposed on the strain generator. The strain gauge includes three or more resistors. With a first direction being a direction in which a blood vessel extends in the measurement site and a second direction being a direction orthogonal to the first direction, the strain generator is attached to the measurement site so that positions of at least three of the resistors in the first direction are different from each other, and the positions of the at least three of the resistors in the second direction are different from each other.

14 Claims, 11 Drawing Sheets

(56) References Cited

U.S. PATENT DOCUMENTS

| | | | |
|---|---|---|---|
| 2017/0086519 A1* | 3/2017 | Vigano' | ............... A63B 71/141 |
| 2018/0184920 A1 | 7/2018 | Rabinovich et al. | |
| 2019/0046050 A1 | 2/2019 | Kato et al. | |
| 2020/0100859 A1 | 4/2020 | Shen et al. | |
| 2021/0063258 A1* | 3/2021 | Sato | ........................ H05K 1/167 |
| 2021/0228102 A1* | 7/2021 | Li | ......................... A61B 5/681 |

FOREIGN PATENT DOCUMENTS

| | | | |
|---|---|---|---|
| JP | 2006-020823 | 1/2006 | |
| JP | 2017-196192 | 11/2017 | |
| JP | 2019-078726 | 5/2019 | |
| JP | 2020-503938 | 2/2020 | |
| WO | WO-2019082978 A1 * | 5/2019 | ............... G01B 7/20 |

\* cited by examiner

VITAL SENSOR

TECHNICAL FIELD

The present invention relates to vital sensors.

BACKGROUND ART

Pulse wave sensors configured to detect pulse waves occurring in accordance with pumping-out of blood by the heart are known. One example is a pulse wave sensor including a pressure-receiving plate to become a strain generator that is supported so as to be bendable by the action of an external force; and a piezoelectric conversion unit configured to convert bending of the pressure-receiving plate to an electric signal. This pulse wave sensor is formed into a dome shape in which a flexible region of the pressure-receiving plate forms a curved surface that projects outward. In an inner surface of the top in the pressure-receiving plate, a pressure-detecting element is provided as the piezoelectric conversion unit (see, for example, Patent Literature 1).

CITATION LIST

Patent Literature

Patent Literature 1: Japanese Laid-Open Patent Publication No. 2002-78689

SUMMARY OF INVENTION

Problem to be Solved by Invention

However, there is a need for a vital sensor that can measure not only the pulse wave but also the dilation direction, the contraction direction, and the like of a blood vessel.

The present invention has been made in view of the above, and it is an object of the present invention to provide a vital sensor configured to detect not only the pulse wave but also the dilation direction and the contraction direction of a blood vessel.

Means for Solving Problem

The present vital sensor is a vital sensor configured to monitor a blood flow, and includes a strain generator to be attached to a measurement site in a subject, and a strain gauge disposed on the strain generator. The strain gauge includes three or more resistors. With a first direction being a direction in which a blood vessel extends in the measurement site and a second direction being a direction orthogonal to the first direction, the strain generator is attached to the measurement site so that positions of at least three of the resistors in the first direction are different from each other, and the positions of the at least three of the resistors in the second direction are different from each other.

Effects of Invention

According to the disclosed technique, it is possible to provide a vital sensor configured to detect not only the pulse wave but also the dilation direction and the contraction direction of a blood vessel.

DESCRIPTION OF EMBODIMENTS

Figure 1:
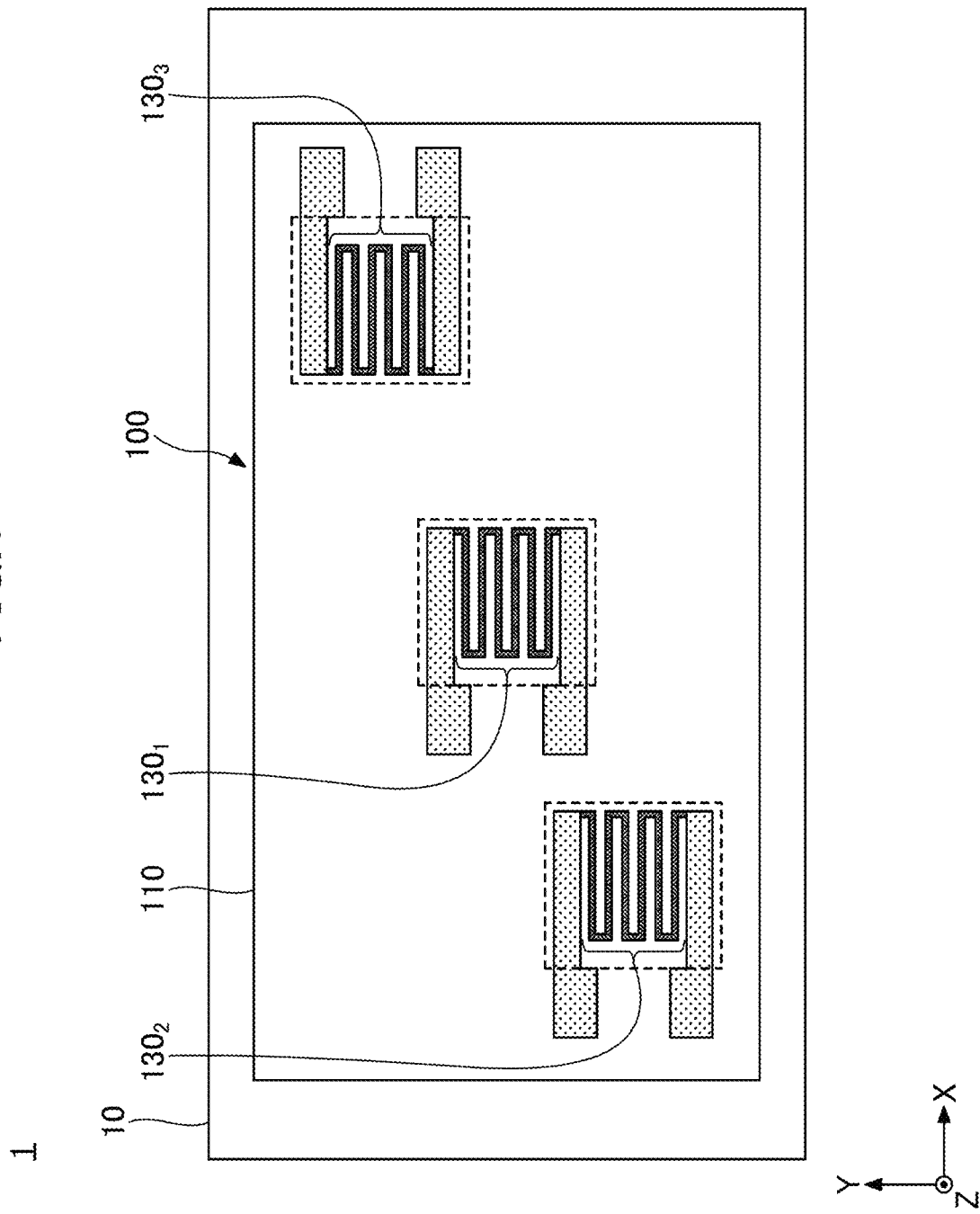
FIG. 1 is a plan view illustrating a vital sensor according to a first embodiment.

Hereinafter, embodiments for carrying out the invention will be described with reference to the drawings. In the drawings, the same symbols denote the same components, and duplicate description thereof may be omitted.

First Embodiment

[Vital Sensor]

FIG. 1 is a plan view illustrating the vital sensor according to the first embodiment. As illustrated in FIG. 1, a vital sensor 1 includes a strain generator 10 to be attached to a measurement site in a subject, and a strain gauge 100 disposed on the strain generator 10.

The strain generator 10 has, for example, a rectangular shape in a plan view thereof. The size of the strain generator 10 may be, for example, about 10 mm long× about 15 mm wide× about 0.1 mm thick. The material usable for the strain generator 10 may be, for example, SUS (stainless steel), copper, aluminum, or the like.

The strain gauge 100 includes, on a substrate 110, a first resistor $130_1$, a second resistor $130_2$, and a third resistor $130_3$ that are to become sensitive portions. For example, the first resistor $130_1$, the second resistor $130_2$, and the third resistor $130_3$ have the same shape in a plan view thereof. As used herein, the same shape also encompasses that shape disposed rotationally symmetrically.

The first resistor $130_1$, the second resistor $130_2$, and the third resistor $130_3$ are disposed on the substrate 110, with longitudinal directions thereof (grid direction described below) being oriented in the same direction. In FIG. 1, the grid direction is an X direction, and a grid width direction orthogonal to the grid direction is a Y direction. Also, a direction orthogonal to the X direction and the Y direction (a thickness direction of the strain generator 10) is a Z direction.

The positions of the first resistor $130_1$, the second resistor $130_2$, and the third resistor $130_3$ in the grid direction are different from each other, and the positions of the first resistor $130_1$, the second resistor $130_2$, and the third resistor $130_3$ in a direction orthogonal to the grid direction are different from each other. Note that, the position of each resistor refers, in a plan view thereof, to a position of the centroid of a region of the substrate 110 where the resistor is formed (hereinafter this region is referred to as a resistor-formed region). That is, the X coordinates and the Y coordinates of the centroids of the resistor-formed regions of the first resistor $130_1$, the second resistor $130_2$, and the third resistor $130_3$ are all different.

For example, the first resistor $130_1$, the second resistor $130_2$, and the third resistor $130_3$ are disposed at constant intervals with respect to the grid direction. That is, for example, the distance between the first resistor $130_1$ and the second resistor $130_2$ in the X direction and the distance between the first resistor $130_1$ and the third resistor $130_3$ in the X direction are equal to each other.

For example, the first resistor $130_1$, the second resistor $130_2$, and the third resistor $130_3$ are also disposed at constant intervals with respect to the direction orthogonal to the grid direction. That is, for example, the distance between the first resistor $130_1$ and the second resistor $130_2$ in the Y direction and the distance between the first resistor $130_1$ and the third resistor $130_3$ in the Y direction are also equal to each other.

Note that, the interval (distance) between the resistors refers, in a plan view thereof, to an interval (distance) between the centroids of the resistor-formed regions of the resistors. Also, the distances being equal to each other includes a case in which the shorter distance is equal to or more than 90% of the longer distance.

The second resistor $130_2$ and the third resistor $130_3$ are disposed to face each other via the first resistor $130_1$ in a direction tilted with respect to the grid direction. As used herein, the second resistor $130_2$ and the third resistor $130_3$ being disposed to face each other via the first resistor $130_1$ means that in a plan view thereof, a straight line connecting the centroid of the resistor-formed region of the second resistor $130_2$ and the centroid of the resistor-formed region of the third resistor $130_3$ passes through a given part of the first resistor $130_1$.

Figure 2:
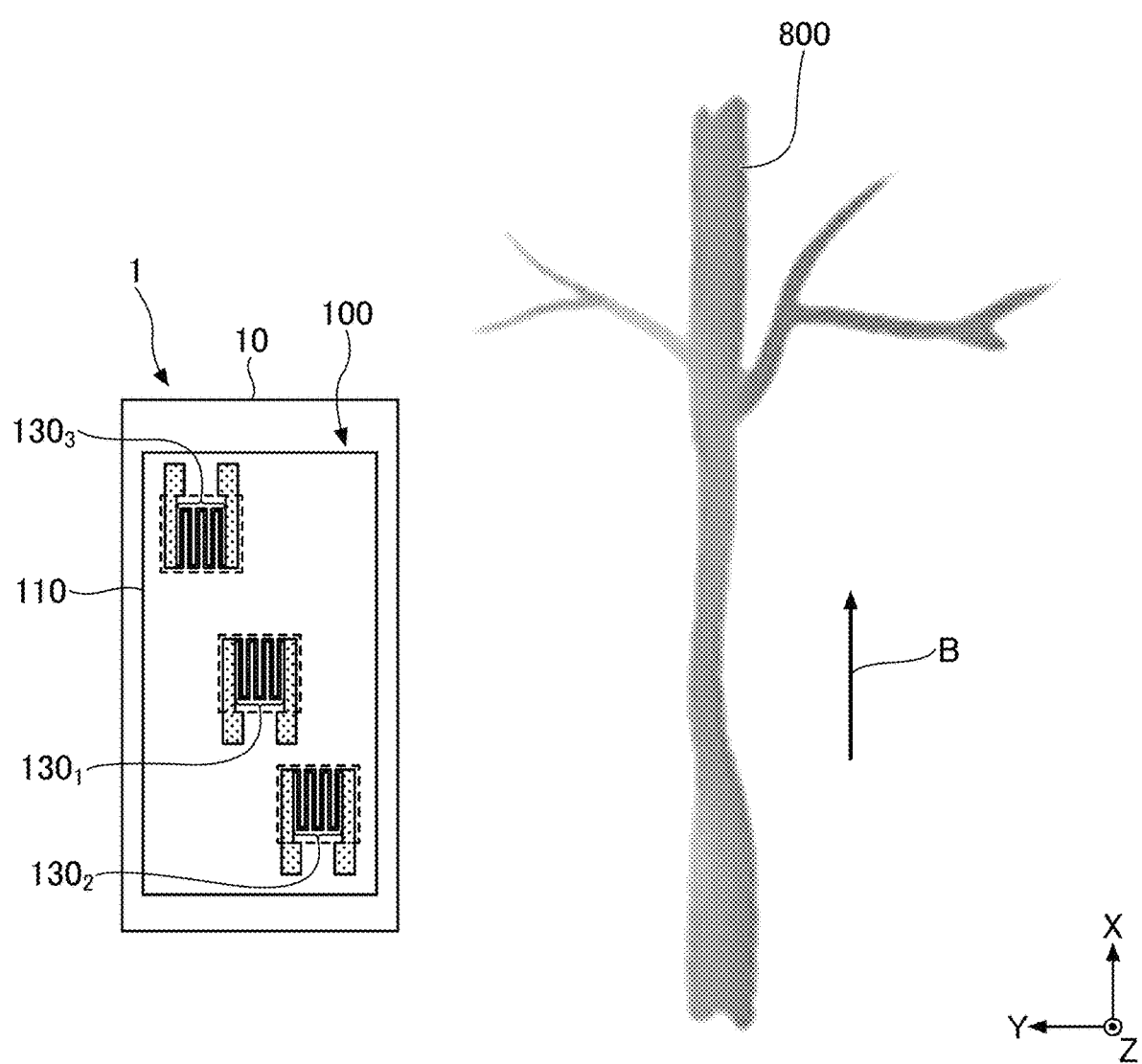
FIG. 2 is a view schematically illustrating a status in which the vital sensor according to the first embodiment monitors a blood flow of a subject (part 1).
Figure 3:
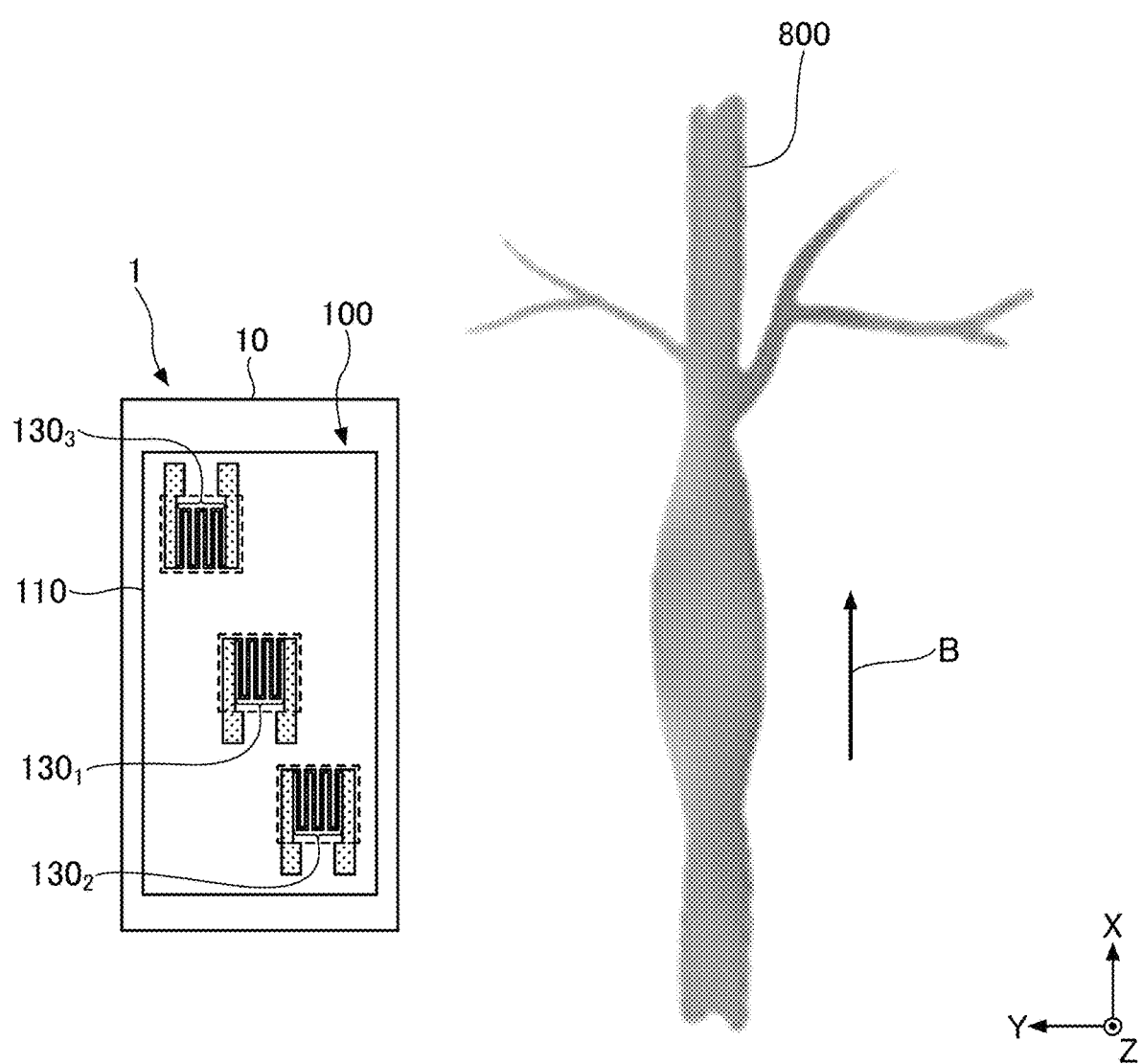
FIG. 3 is a view schematically illustrating a status in which the vital sensor according to the first embodiment monitors a blood flow of a subject (part 2).

FIG. 2 and FIG. 3 are each a view schematically illustrating a status in which the vital sensor according to the first embodiment monitors the blood flow of the subject. FIG. 2 schematically illustrates a status in which a blood vessel 800 is contracted, and FIG. 3 schematically illustrates a status in which the blood vessel 800 is dilated. Arrow B in FIG. 2 and FIG. 3 indicates a direction in which the blood vessel 800 extends in the measurement site in the subject, and also a direction in which the blood flows.

The vital sensor 1 is a sensor configured to monitor the blood flow, and is, for example, attached to the wrist of the subject so that the lower surface of the strain generator 10 contacts the radial artery of the subject. That is, the measurement site in the subject is, for example, the wrist of the subject.

The strain generator 10 is attached to the measurement site in the subject so that the positions of the first resistor $130_1$, the second resistor $130_2$, and the third resistor $130_3$ in a direction indicated by the arrow B, in which the blood vessel extends, are different from each other, and the positions of the first resistor $130_1$, the second resistor $130_2$, and the third resistor $130_3$ in a direction orthogonal to the direction indicated by the arrow B are different from each other. For example, the strain generator 10 is attached to the measurement site in the subject so that the X direction, which is the grid direction, coincides with the direction indicated by the arrow B. That is, for example, the strain generator 10 is attached to the measurement site in the subject so that the first resistor $130_1$, the second resistor $130_2$, and the third resistor $130_3$ are disposed with the grid direction thereof being oriented in the direction indicated by the arrow B.

Note in FIG. 2 and FIG. 3 that, for the sake of convenience, the vital sensor 1 is enlarged for illustration. However, the vital sensor 1 is formed to have such a size that all of the first resistor $130_1$, the second resistor $130_2$, and the third resistor $130_3$ are positioned on the blood vessel 800. In the strain gauge 100, the size of each resistor-formed region may be, for example, a square of about 0.3 mm per side.

When the strain generator 10 is attached to the measurement site in the subject, for example, the first resistor $130_1$ is disposed on the center line of the blood vessel 800 and the vicinity thereof, with the grid direction thereof being oriented in the direction indicated by the arrow B. Also, the second resistor $130_2$ is disposed at one side of the first resistor 130: in the direction indicated by the arrow B (−X side in FIG. 2 and FIG. 3) and one side of the first resistor $130_1$ in the direction orthogonal to the direction indicated by the arrow B (−Y side in FIG. 2 and FIG. 3).

Also, the third resistor $130_3$ is disposed at the other side of the first resistor $130_1$ in the direction indicated by the arrow B (+X side in FIG. 2 and FIG. 3) and the other side of the first resistor $130_1$ in the direction orthogonal to the direction indicated by the arrow B (+Y side in FIG. 2 and FIG. 3). That is, the second resistor $130_2$ and the third resistor $130_3$ are disposed to face each other via the first resistor $130_1$ in the direction tilted with respect to the direction indicated by the arrow B.

The first resistor $130_1$, the second resistor $130_2$, and the third resistor $130_3$ are disposed, for example, at constant intervals with respect to the grid direction. Also, the first resistor $130_1$, the second resistor $130_2$, and the third resistor $130_3$ are disposed, for example, at constant intervals with respect to the direction orthogonal to the grid direction.

The blood vessel 800 repeats contraction and dilation in accordance with pulse waves. The vital sensor 1 is attached to the measurement site in the subject so that the positions of the first resistor $130_1$, the second resistor $130_2$, and the third resistor $130_3$ in the direction indicated by the arrow B are different from each other, and the positions of the first resistor $130_1$, the second resistor $130_2$, and the third resistor $130_3$ in the direction orthogonal to the direction indicated by the arrow B are different from each other. Therefore, based on changes in outputs of the first resistor $130_1$, the second resistor $130_2$, and the third resistor $130_3$, the vital sensor 1 can detect pulse waves, and also can detect change in the blood flow rate in the blood vessel 800 and the dilation direction and the contraction direction of the blood vessel 800.

Also, the vital sensor 1 monitors the blood flow with the strain gauge, and thus can realize an inexpensive wearable vital sensor compared to an optical sensor based on change in absorption characteristics of oxyhemoglobin in the blood vessel, an optical fiber FBG sensor (Fiber Bragg Grating sensor) that is expensive and cumbersome, and the like. Especially, when a Cr mixed-phase film described below is used as the resistor, it is possible to realize a wearable vital sensor that is inexpensive, compact, and high in accuracy.

Hereinafter, the strain gauge 100 will be described in detail. Note that, when there is no particular need for distinction, the first resistor $130_1$, the second resistor $130_2$, and the third resistor $130_3$ may be collectively referred to as a resistor 130.

Figure 4:
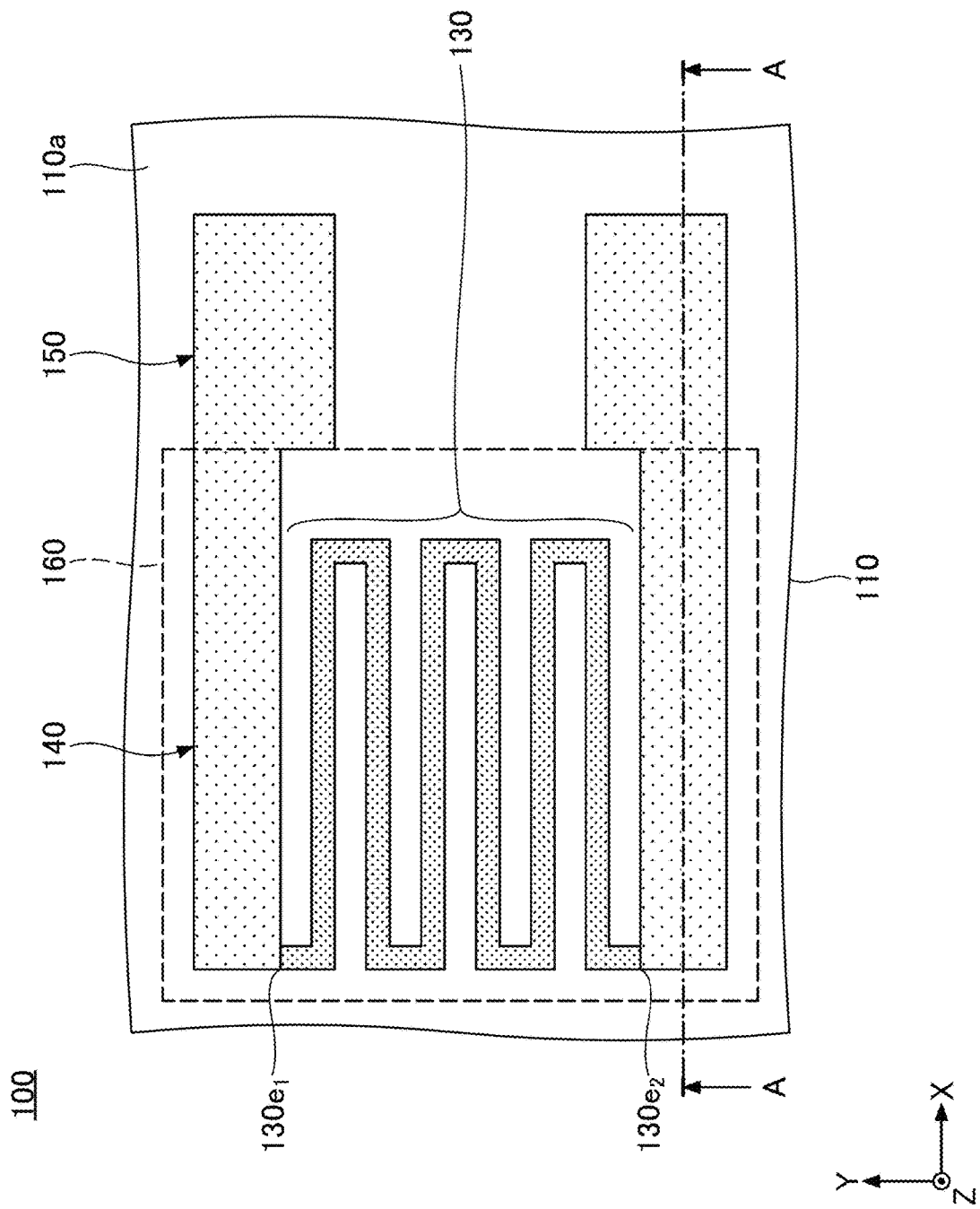
FIG. 4 is a plan view of one resistor, and the vicinity thereof, of a strain gauge according to the first embodiment.
Figure 5:
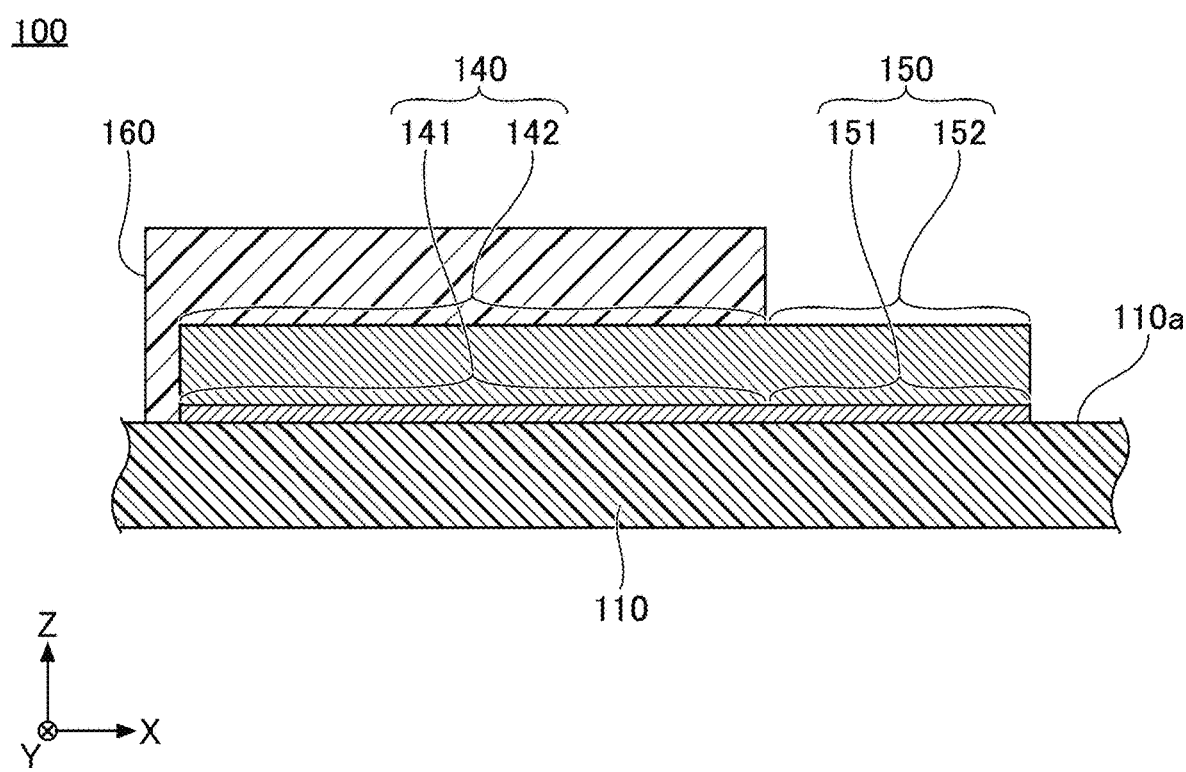
FIG. 5 is a cross-sectional view of one resistor, and the vicinity thereof, of a strain gauge according to the first embodiment.

FIG. 4 is a plan view of one resistor, and the vicinity thereof, of the strain gauge according to the first embodiment. FIG. 5 is a cross-sectional view of one resistor, and the vicinity thereof, of the strain gauge according to the first embodiment, and illustrates a cross section thereof along line A-A in FIG. 4. As illustrated in FIG. 1, FIG. 4, and FIG. 5, the strain gauge 100 includes three sets each including the resistor 130, an interconnect 140, an electrode 150, and a cover layer 160, and these sets are disposed on the single substrate 110. However, unlike in FIG. 1, three strain gauges each including, on the single substrate 110, one set including the resistor 130, the interconnect 140, the electrode 150, and the cover layer 160 may be disposed on the strain generator 10. Note in FIG. 4 that, for the sake of convenience, only the outer edge of the cover layer 160 is illustrated with a dashed line. The cover layer 160 may be provided according to the needs.

Note in FIG. 4 and FIG. 5 that, for the sake of convenience, in the strain gauge 100, a side of the substrate 110 at which the resistor 130 is provided is defined as an upper side or one side, and a side of the substrate 110 at which the resistor 130 is not provided is defined as a lower side or the other side. Also, a surface of each site on which the resistor 130 is provided is defined as one surface or an upper surface, and a surface of each site on which the resistor 130 is not provided is defined as the other surface or a lower surface. However, the strain gauge 100 can be used upside down or can be disposed at a given angle. Also, the plan view refers to viewing an object from the direction normal to an upper surface 110a of the substrate 110, and a planar shape refers to a shape observed by viewing the object from the direction normal to the upper surface 110a of the substrate 110.

The substrate 110 is a member to become a base layer for forming the resistor 130 and the like, and has flexibility. No particular limitation is imposed on the thickness of the substrate 110, which may be appropriately selected in accordance with the intended purpose. However, for example, the thickness of the substrate 110 may be from about 5 µm through about 500 µm. Especially, the substrate 110 having a thickness of from 5 µm through 200 µm is preferable in terms of transmittivity of strain from the surface of the strain generator bonded to the lower surface of the substrate 110 via an adhesive layer or the like, and in terms of dimensional stability to the environment. The substrate 110 having a thickness of 10 µm or more is further preferable in terms of insulating property.

The substrate 110 can be formed of an insulating resin film such as a PI (polyimide) resin, an epoxy resin, a PEEK (polyether ether ketone) resin, a PEN (polyethylene naphthalate) resin, a PET (polyethylene terephthalate) resin, a PPS (polyphenylene sulfide) resin, a LCP (liquid crystal polymer) resin, a polyolefin resin, or the like. Note that, the film refers to a flexible member having a thickness of about 500 µm or less.

As used herein, being "formed of an insulating resin film" is not intended to preclude the substrate 110 from containing fillers, impurities, or the like in the insulating resin film. The substrate 110 may be formed of, for example, an insulating resin film containing a filler such as silica, alumina, or the like.

Except for the resins, examples of the material of the substrate 110 include: crystalline materials such as $SiO_2$, $ZrO_2$ (including YSZ), Si, $Si_2N_3$, $Al_2O_3$ (including sapphire), ZnO, perovskite ceramics ($CaTiO_3$, $BaTiO_3$), and the like. Further examples thereof include glass that is amorphous, and the like. As the material of the substrate 110, metals such as aluminum, an aluminum alloy (duralumin), titanium, or the like may be used. In this case, for example, an insulating film is formed on the substrate 110 that is formed of the metal.

The resistor 130 is a thin film formed on the substrate 110 in a predetermined pattern, and is a sensitive portion that changes in resistance by receiving strain. The resistor 130 may be directly formed on the upper surface 110a of the substrate 110, or may be formed via another layer at the upper surface 110a of the substrate 110. Note in FIG. 4 that, for the sake of convenience, the resistor 130 is illustrated with a thick mat pattern.

The resistor 130 is a structure in which a plurality of elongated portions are disposed at predetermined intervals such that longitudinal directions thereof are oriented in the same direction (the direction along the line A-A in FIG. 4 (X direction)) and the ends of the elongated portions next to each other are connected together in a staggered manner. As a whole, the structure is folded back in a zigzag manner. The longitudinal directions of the plurality of elongated portions are the grid direction, and a direction perpendicular to the grid direction is the grid width direction (the direction perpendicular to the line A-A in FIG. 4 (Y direction)).

The longitudinal ends of the outermost two elongated portions in the grid width direction are bent in the grid width direction, and form terminals $130e_1$ and $130e_2$ of the resistor 130 in the grid width direction. The terminals $130e_1$ and $130e_2$ of the resistor 130 in the grid width direction are electrically connected to the electrodes 150 via the interconnects 140. In other words, the interconnects 140 electrically connect the terminals $130e_1$ and $130e_2$ of the resistor 130 in the grid width direction, to the electrodes 150.

The resistor 130 can be formed of, for example, a Cr (chromium)-containing material, a Ni (nickel)-containing material, or a material containing both of Cr and Ni. That is, the resistor 130 can be formed of a material containing Cr, Ni, or both. Examples of the Cr-containing material include Cr mixed-phase films. Examples of the Ni-containing material include Cu—Ni (copper nickel). Examples of the material containing both of Cr and Ni include Ni—Cr (nickel chromium).

As used herein, the Cr mixed-phase film is a film in which Cr, CrN, $Cr_2N$, are the like are phase-mixed. The Cr mixed-phase film may contain unavoidable impurities such as chromium oxide and the like.

No particular limitation is imposed on the thickness of the resistor 130, which may be appropriately selected in accordance with the intended purpose. However, for example, the thickness thereof can be from about 0.05 µm through about 2 µm. Especially, the resistor 130 having a thickness of 0.1 µm or more is preferable in terms of an increase in the crystallinity of crystals forming the resistor 130 (e.g., the crystallinity of α-Cr). Also, the resistor 130 having a thickness of 1 µm or less is further preferable in terms of being able to reduce cracks of a film forming the resistor 130 due to internal stress of that film, and warping from the substrate 110. The width of the resistor 130 can be, for example, from about 10 µm through about 100 µm in terms of optimization for required specifications such as resistivity, transverse sensitivity, and the like, and also in consideration of measures against disconnection.

For example, when the resistor 130 is the Cr mixed-phase film, by employing α-Cr (alpha-chromium), which is a stable crystal phase, as a main component, it is possible to increase stability of gauge characteristics. Also, when the resistor 130 contains α-Cr as a main component, the gauge factor of the strain gauge 100 can be 10 or more, and a temperature coefficient of the gauge factor, TCS, and a temperature coefficient of resistance, TCR, can be within the range of from −1000 ppm/° ° C. through +1000 ppm/° C. As used herein, the main component means that a substance of interest accounts for 50% by weight or more of all of the substances forming the resistor. However, from the viewpoint of increasing gauge characteristics, the resistor 130 preferably contains α-Cr in an amount of 80% by weight or more and further preferably in an amount of 90% by weight or more. Note that, α-Cr is Cr of a bcc structure (body-centered cubic structure).

Also, when the resistor 130 is the Cr mixed-phase film, CrN and $Cr_2N$ contained in the Cr mixed-phase film are preferably 20% by weight or less. When CrN and $Cr_2N$ contained in the Cr mixed-phase film are 20% by weight or less, it is possible to suppress reduction in gauge factor.

Also, the percentage of $Cr_2N$ in CrN and $Cr_2N$ is preferably 80% by weight or more and less than 90% by weight, and further preferably 90% by weight or more and less than 95% by weight. When the percentage of $Cr_2N$ in CrN and $Cr_2N$ is 90% by weight or more and less than 95% by weight, the presence of $Cr_2N$, which has semi-conductive properties, makes reduction in TCR (negative TCR) further significant. Moreover, formation into ceramics is reduced, and thus brittle fracture is reduced.

Meanwhile, when a trace amount of $N_2$ or atomic N is included or present in the film, release thereof outward of the film is caused by the external environments (e.g., under high-temperature environments), thereby causing change in the film stress. By creating chemically stable CrN, the above-described unstable N is not generated, and a stable strain gauge can be obtained.

The interconnect 140 is formed on the substrate 110, and is electrically connected to the resistor 130 and the electrode 150. The interconnect 140 includes a first metallic layer 141 and a second metallic layer 142 stacked on the upper surface of the first metallic layer 141. The interconnect 140 is not limited to be in the form of a straight line, and may be formed into a given pattern. Also, the interconnect 140 may have a given width and a given length. Note in FIG. 4 that, for the sake of convenience, the interconnect 140 and the electrode 150 are illustrated with a mat pattern thinner than in the resistor 130.

The electrode 150 is formed on the substrate 110 and is electrically connected to the resistor 130 via the interconnect 140. For example, the electrode 150 is formed into an approximately rectangular shape that is wider than the interconnect 140. The electrode 150 is a pair of electrodes configured to output, to the exterior, change in resistivity of the resistor 130 caused by strain. For example, a lead wire for external connection is bonded to the electrode 150.

The electrode 150 includes a pair of first metallic layers 151 and second metallic layers 152 that are stacked on the upper surfaces of the first metallic layers 151. The first metallic layers 151 are electrically connected to the terminals $130e_1$ and $130e_2$ of the resistor 130 via the first metallic layers 141 of the interconnect 140. The first metallic layer 151 is formed into an approximately rectangular shape in a plan view thereof. The first metallic layer 151 may be formed to have the same width as the interconnect 140.

Note that, the resistor 130, the first metallic layer 141, and the first metallic layer 151 are denoted by different reference numerals for the sake of convenience. However, these can be integrally formed of the same material in the same step. Therefore, the resistor 130, the first metallic layer 141, and the first metallic layer 151 have approximately the same thickness. Also, the second metallic layer 142 and the second metallic layer 152 are denoted by different reference numerals for the sake of convenience. However, these can be integrally formed of the same material in the same step. Therefore, the second metallic layer 142 and the second metallic layer 152 have approximately the same thickness.

The second metallic layers 142 and 152 are formed of a material having resistance lower than in the resistor 130 (the first metallic layers 141 and 151). No particular limitation is imposed on the material of the second metallic layers 142 and 152, which may be appropriately selected in accordance with the intended purpose, as long as the material of the second metallic layers 142 and 152 is a material having resistance lower than in the resistor 130. For example, when the resistor 130 is the Cr mixed-phase film, examples of the material of the second metallic layers 142 and 152 include: Cu, Ni, Al, Ag, Au, Pt, and the like; alloys of any one metal of the foregoing; compounds of any one metal of the foregoing; and stacked films obtained by appropriately stacking any one of the foregoing metals, alloys, and compounds. No particular limitation is imposed on the thickness of the second metallic layers 142 and 152, which may be appropriately selected in accordance with the intended purpose. For example, the thickness thereof can be from about 3 μm through about 5 μm.

The second metallic layers 142 and 152 may be formed on parts of the upper surfaces of the first metallic layers 141 and 151, or may be formed on the entirety of the upper surfaces of the first metallic layers 141 and 151. On the upper surface of the second metallic layer 152, one or more other metallic layers may be further stacked. For example, the second metallic layer 152 is a copper layer, and a gold layer may be stacked on the upper surface of the copper layer. Alternatively, the second metallic layer 152 is a copper layer, and a palladium layer and a gold layer may be sequentially stacked on the upper surface of the copper layer. When the uppermost layer of the electrode 150 is a gold layer, it is possible to increase solder wettability of the electrode 150.

In this way, the interconnect 140 has a structure in which the second metallic layer 142 is stacked on the first metallic layer 141 formed of the same material as in the resistor 130. Therefore, the interconnect 140 has resistance lower than the resistor 130, and thus the interconnect 140 can be suppressed from functioning as the resistor. As a result, it is possible to increase strain detection accuracy by the resistor 130.

In other words, by providing the interconnect 140 having resistance lower than the resistor 130, a substantially sensitive portion of the strain gauge 100 can be limited to a local region where the resistor 130 is formed. Therefore, it is possible to increase strain detection accuracy by the resistor 130.

Especially, for a high-sensitive strain gauge having a gauge factor of 10 or more using the Cr mixed-phase film as the resistor 130, the significant effect of increasing strain detection accuracy is produced by lowering the resistance of the interconnect 140 relative to the resistor 130 and limiting the substantially sensitive portion to the local region where the resistor 130 is formed. Also, the effect of reducing transverse sensitivity is produced by lowering the resistance of the interconnect 140 relative to the resistor 130.

Note that, the routing pattern of the interconnect 140 and the position of the electrode 150 can be appropriately set. For example, the electrodes 150 to be connected to the resistors may be aligned in a row at predetermined positions.

The cover layer 160 is formed at the substrate 110, and covers the resistor 130 and the interconnect 140 and exposes the electrode 150. A part of the interconnect 140 may be exposed from the cover layer 160. By providing the cover layer 160 covering the resistor 130 and the interconnect 140, it is possible to prevent the resistor 130 and the interconnect 140 from receiving mechanical damage and the like. Also, by providing the cover layer 160, it is possible to protect the resistor 130 and the interconnect 140 from moisture and the like. Note that, the cover layer 160 may be provided so as to cover the entire region excluding the electrode 150.

The cover layer 160 can be formed of an insulating resin such as a PI resin, an epoxy resin, a PEEK resin, a PEN resin, a PET resin, a PPS resin, a composite resin (e.g., a silicone resin or a polyolefin resin), or the like. The cover layer 160 may contain a filler or a pigment. No particular limitation is imposed on the thickness of the cover layer 160, which may be appropriately selected in accordance with the intended purpose. However, for example, the thickness thereof can be from about 2 μm through about 30 μm.

In order to produce the strain gauge 100, first, the substrate 110 is provided, and a metallic layer (which is referred to as metallic layer A for the sake of convenience) is formed on the upper surface 110a of the substrate 110. The metallic layer A is a layer to be eventually patterned to become the resistor 130, the first metallic layer 141, and the first metallic layer 151. Therefore, the material and the thickness of the metallic layer A are similar to the material and the thickness of the resistor 130, the first metallic layer 141, and the first metallic layer 151.

The metallic layer A can be formed, for example, through magnetron sputtering that uses, as a target, a raw material from which the metallic layer A can be formed. Instead of magnetron sputtering, the metallic layer A may be formed through reactive sputtering, vapor deposition, arc ion plating, pulse laser deposition, or the like.

From the viewpoint of stabilizing gauge characteristics, before formation of the metallic layer A, a functional layer having a predetermined thickness is preferably formed in vacuum as an underlying layer on the upper surface 110a of the substrate 110, for example, through conventional sputtering.

In the present application, the functional layer refers to a layer that has the function of promoting crystal growth of at least the metallic layer A (the resistor 130) that is the upper layer. Preferably, the functional layer further has the function of preventing oxidation of the metallic layer A caused by oxygen and moisture included in the substrate 110, and the function of increasing adhesiveness between the substrate 110 and the metallic layer A. The functional layer may further have other functions.

The insulating resin film that forms the substrate 110 contains oxygen and moisture. Especially, when the metallic layer A contains Cr, it is effective for the functional layer to have the function of preventing oxidation of the metallic layer A because Cr forms an autoxidized film.

No particular limitation is imposed on the material of the functional layer, which may be appropriately selected in accordance with the intended purpose, as long as the selected material has the function of promoting crystal growth of at least the metallic layer A (the resistor 130) that is the upper layer. Examples thereof include one or more types of metals selected from the group consisting of Cr (chromium), Ti (titanium), V (vanadium), Nb (niobium), Ta (tantalum), Ni (nickel), Y (yttrium), Zr (zirconium), Hf (hafnium), Si (silicon), C (carbon), Zn (zinc), Cu (copper), Bi (bismuth), Fe (iron), Mo (molybdenum), W (tungsten), Ru (ruthenium), Rh (rhodium), Re (rhenium), Os (osmium), Ir (iridium), Pt (platinum), Pd (palladium), Ag (silver), Au (gold), Co (cobalt), Mn (manganese), and Al (aluminum); alloys of any one metal of the foregoing group; and compounds of any one metal of the foregoing group.

Examples of the above alloys include FeCr, TiAl, FeNi, NiCr, CrCu, and the like. Also, examples of the above compounds include TiN, TaN, $Si_3N_4$, $TiO_2$, $Ta_2O_5$, $SiO_2$, and the like.

When the functional layer is formed of a conductive material such as a metal or an alloy, the thickness of the functional layer is preferably $1/20$ or less the thickness of the resistor. When the thickness of the functional layer falls within the range as described above, it is possible to promote crystal growth of α-Cr, and also prevent reduction in strain detection sensitivity occurring when a part of a current flowing through the resistor flows through the functional layer.

When the functional layer is formed of a conductive material such as a metal or an alloy, the thickness of the functional layer is more preferably $1/50$ or less the thickness of the resistor. When the thickness of the functional layer falls within the range as described above, it is possible to promote crystal growth of α-Cr, and also further prevent reduction in strain detection sensitivity occurring when a part of a current flowing through the resistor flows through the functional layer.

When the functional layer is formed of a conductive material such as a metal or an alloy, the thickness of the functional layer is further preferably $1/100$ or less the thickness of the resistor. When the thickness of the functional layer falls within the range as described above, it is possible to even further prevent reduction in strain detection sensitivity occurring when a part of a current flowing through the resistor flows through the functional layer.

When the functional layer is formed of an insulating material such as an oxide or a nitride, the thickness of the functional layer is preferably from 1 nm through 1 μm. When the thickness of the functional layer falls within the range as described above, it is possible to promote crystal growth of α-Cr, and also readily form the functional layer without cracks.

When the functional layer is formed of an insulating material such as an oxide or a nitride, the thickness of the functional layer is more preferably from 1 nm through 0.8 μm. When the thickness of the functional layer falls within the range as described above, it is possible to promote crystal growth of α-Cr, and also more readily form the functional layer without cracks.

When the functional layer is formed of an insulating material such as an oxide or a nitride, the thickness of the functional layer is further preferably from 1 nm through 0.5 μm. When the thickness of the functional layer falls within the range as described above, it is possible to promote crystal growth of α-Cr, and also even more readily form the functional layer without cracks.

Note that, for example, the functional layer is patterned into approximately the same planar shape as the planar shape of the resistor as illustrated in FIG. 4. However, the planar shape of the functional layer is not limited to approximately the same planar shape as the planar shape of the resistor. When the functional layer is formed of an insulating material, the functional layer does not need to be patterned into the same planar shape as the planar shape of the resistor. In this case, the functional layer may be formed as a solid pattern on the region where at least the resistor is formed.

Alternatively, the functional layer may be formed in a solid pattern on the entire upper surface of the substrate 110.

Also, when the functional layer is formed of an insulating material, the functional layer is formed relatively thick so as to have a thickness of 50 nm or more and 1 μm or less, and is formed in a solid pattern. Thereby, the thickness and the surface area of the functional layer increase, and thus it is possible to release, toward the substrate 110, heat generated when the resistor generates heat. As a result, reduction in measurement accuracy of the strain gauge 100 due to self-heating of the resistor can be suppressed.

For example, the functional layer can be formed in vacuum through conventional sputtering that uses, as a target, a raw material from which the functional layer can be formed, and in which Ar (argon) gas is introduced into a chamber. By using the conventional sputtering, the functional layer is formed while etching the upper surface 110a of the substrate 110 with Ar. Thus, it is possible to obtain the effect of minimizing the amount of the functional layer and increasing adhesiveness.

However, this is one example of the forming methods for the functional layer, and the functional layer may be formed by other methods. In one of the other methods, the upper surface 110a of the substrate 110 is activated with a plasma treatment or the like using, for example, Ar performed before formation of the functional layer, thereby obtaining the effect of increasing adhesiveness. Subsequently, the functional layer is formed in vacuum through magnetron sputtering.

No particular limitation is imposed on combination of the material of the functional layer and the material of the metallic layer A, and the combination thereof may be appropriately selected. However, for example, the functional layer can be formed of Ti, and the Cr mixed-phase film containing α-Cr (alpha-chromium) as the main component can be formed as the metallic layer A.

In this case, for example, the metallic layer A can be formed through magnetron sputtering that uses, as a target, a raw material from which the Cr mixed-phase film can be formed, and in which Ar gas is introduced into a chamber. Alternatively, the metallic layer A may be formed through reactive sputtering by using pure Cr as a target and introducing Ar gas and an appropriate amount of nitrogen gas into a chamber. At this time, by changing the amount of the nitrogen gas to be introduced and the pressure thereof (partial pressure of nitrogen) or providing a heating step of adjusting the heating temperature, it is possible to adjust the percentages of CrN and $Cr_2N$ contained in the Cr mixed-phase film, and the percentage of $Cr_2N$ in CrN and $Cr_2N$.

In these methods, the growth plane of the Cr mixed-phase film is defined owing to the functional layer formed of Ti, and the Cr mixed-phase film containing α-Cr of a stable crystal structure as the main component can be formed. Also, when Ti forming the functional layer is diffused in the Cr mixed-phase film, the resulting gauge characteristics increase. For example, the gauge factor of the strain gauge 100 can be 10 or more, and the temperature coefficient of the gauge factor, TCS, and the temperature coefficient of resistance, TCR, can be within the range of from −1000 ppm/° C. through +1000 ppm/° C. Note that, when the functional layer is formed of Ti, Ti and TiN (titanium nitride) may be contained in the Cr mixed-phase film.

Note that, when the metallic layer A is the Cr mixed-phase film, the functional layer formed of Ti has all of the function of promoting crystal growth of the metallic layer A, the function of preventing oxidation of the metallic layer A caused by oxygen and moisture included in the substrate 110, and the function of increasing adhesiveness between the substrate 110 and the metallic layer A. The same applies to when Ta, Si, Al, or Fe is used as the functional layer instead of Ti.

In this way, by providing the functional layer as a lower layer of the metallic layer A, it is possible to promote crystal growth of the metallic layer A and produce the metallic layer A formed of a stable crystal phase. As a result, the stability of the gauge characteristics of the strain gauge 100 can be increased. Also, because the material forming the functional layer is diffused in the metallic layer A, the gauge characteristics of the strain gauge 100 can be increased.

Next, the second metallic layer 142 and the second metallic layer 152 are formed on the upper surface of the metallic layer A. The second metallic layer 142 and the second metallic layer 152 can be formed, for example, through photolithography.

Specifically, first, a seed layer is formed, for example, through sputtering, electroless plating, or the like so as to cover the upper surface of the metallic layer A. Next, a photosensitive resist is formed on the entirety of the upper surface of the seed layer, followed by exposure to light and development, thereby forming an aperture that exposes therefrom a region for forming the second metallic layer 142 and the second metallic layer 152. At this time, by adjusting the shape of the aperture of the resist, the pattern of the second metallic layer 142 can have a given shape. As the resist, for example, a dry film resist or the like can be used.

Next, for example, through electrolytic plating that uses the seed layer as a power supply path, the second metallic layer 142 and the second metallic layer 152 are formed on the seed layer that is exposed in the aperture. The electrolytic plating is suitable because the electrolytic plating has a high takt, and can form a low-stress electrolytic-plated layer as the second metallic layer 142 and the second metallic layer 152. By forming a thick electrolytic-plated layer having low stress, it is possible to prevent occurrence of warping of the strain gauge 100. Note that, the second metallic layer 142 and the second metallic layer 152 may be formed through electroless plating.

Next, the resist is removed. The resist can be removed, for example, through immersion in a solution that can dissolve the material of the resist.

Next, a photosensitive resist is formed on the entirety of the upper surface of the seed layer, followed by exposure to light and development, thereby performing patterning in a planar shape similar to the resistor 130, the interconnect 140, and the electrode 150 of FIG. 4. As the resist, for example, a dry film resist or the like can be used. Then, using the resist as an etching mask, the metallic layer A and the seed layer exposed from the resist are removed, thereby forming the resistor 130, the interconnect 140, and the electrode 150 having the planar shapes of FIG. 4.

For example, it is possible to remove unnecessary portions of the metallic layer A and the seed layer through wet etching. When the functional layer is formed as the lower layer of the metallic layer A, the functional layer is patterned through etching into the planar shapes as illustrated in FIG. 4, similar to the resistor 130, the interconnect 140, and the electrode 150. Note that, at this time, the seed layer is formed on the resistor 130, the first metallic layer 141, and the first metallic layer 151.

Next, using the second metallic layer 142 and the second metallic layer 152 as an etching mask, by removing the unnecessary seed layer exposed from the second metallic layer 142 and the second metallic layer 152, the second metallic layer 142 and the second metallic layer 152 are formed. Note that, the seed layer directly below the second metallic layer 142 and the second metallic layer 152 remains. For example, through wet etching using an etching solution that etches the seed layer and does not etch the functional layer, the resistor 130, the interconnect 140, and the electrode 150, the unnecessary seed layer can be removed.

Subsequently, if necessary, by providing the upper surface 110a of the substrate 110 with the cover layer 160 that covers the resistor 130 and the interconnect 140 and exposes the electrode 150, the strain gauge 100 is completed. For example, the cover layer 160 can be produced by laminating a semi-cured thermosetting insulating resin film on the upper surface 110a of the substrate 110 so as to cover the resistor 130 and the interconnect 140 and expose the electrode 150, followed by heating for curing. The cover layer 160 may be produced by applying a liquid or paste-form thermosetting insulating resin on the upper surface 110a of the substrate 110 so as to cover the resistor 130 and the interconnect 140 and expose the electrode 150, followed by heating for curing.

Modified Example 1 of the First Embodiment

Modified Example 1 of the first embodiment illustrates an example of a vital sensor including a strain gauge in which the disposition of resistors is different from the disposition of the resistors in the first embodiment. Note that, in Modified Example 1 of the first embodiment, description of the same components as in the above-described embodiment may be omitted.

Figure 6:
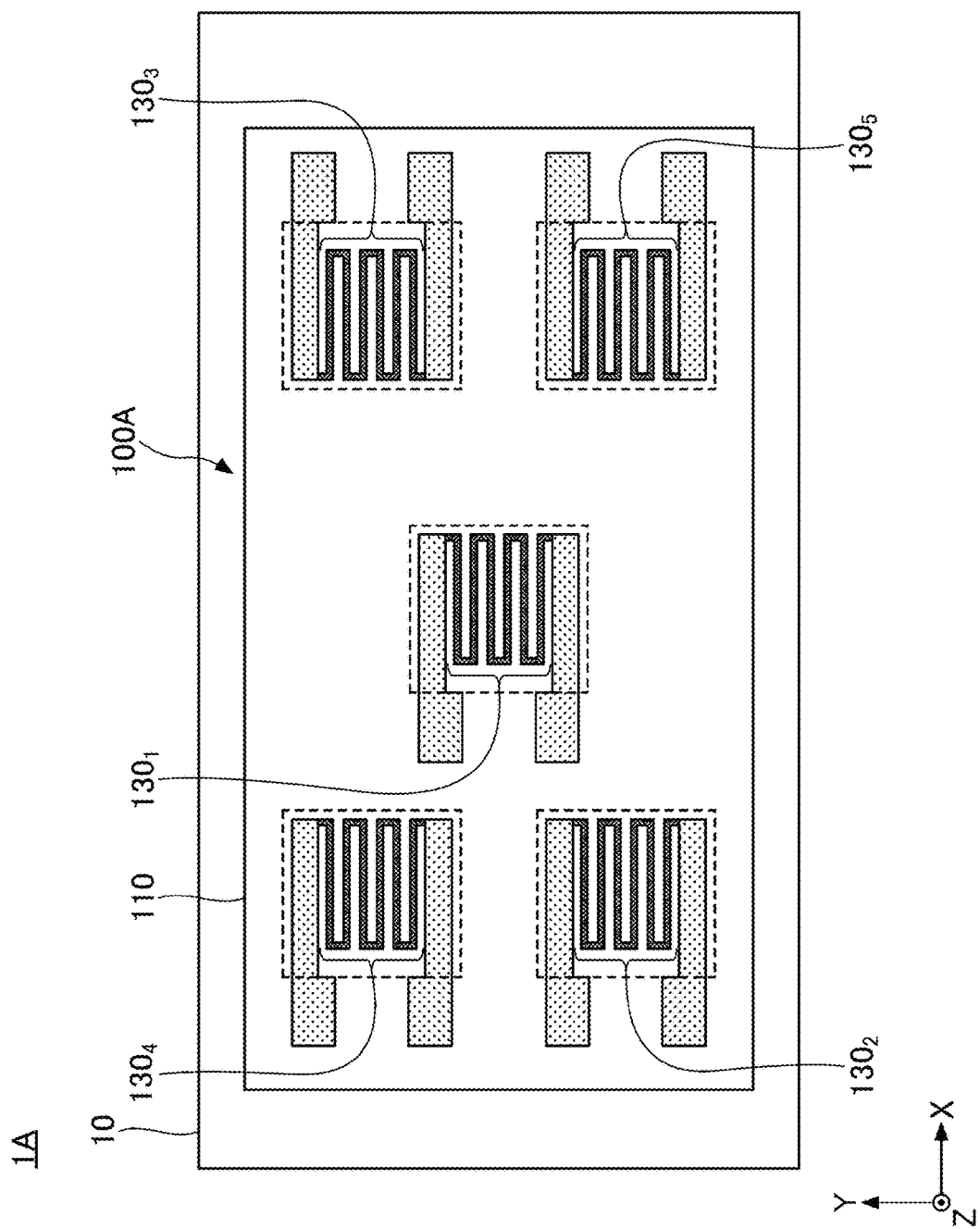
FIG. 6 is a plan view illustrating a vital sensor according to Modified Example 1 of the first embodiment.

FIG. 6 is a plan view illustrating a vital sensor according to Modified Example 1 of the first embodiment. As illustrated in FIG. 6, a vital sensor 1A is different from the vital sensor 1 in that the strain gauge 100 is replaced with a strain gauge 100A. The strain gauge 100A is different from the strain gauge 100 in that a fourth resistor $130_4$ and a fifth resistor $130_5$ are added. The fourth resistor $130_4$ and the fifth resistor $130_5$ are disposed so that the grid direction thereof is oriented in the X direction.

The fourth resistor $130_4$ is the same as the second resistor $130_2$ in terms of the position thereof in the grid direction and is the same as the third resistor $130_3$ in terms of the position thereof in the direction orthogonal to the grid direction. The fifth resistor $130_5$ is the same as the third resistor $130_3$ in terms of the position thereof in the grid direction and is the same as the second resistor $130_2$ in terms of the position thereof in the direction orthogonal to the grid direction. The fourth resistor $130_4$ and the fifth resistor $130_5$ are disposed to face each other via the first resistor $130_1$ in the direction tilted with respect to the grid direction.

In this way, by the addition of the fourth resistor $130_4$ and the fifth resistor $130_5$, outputs from the fourth resistor $130_4$ and the fifth resistor $130_5$ can be obtained. Therefore, when the vital sensor 1A is attached to the measurement site in the subject, it is possible to increase detection accuracy of pulse waves, change in the blood flow rate in the blood vessel, and the dilation direction and the contraction direction of the blood vessel.

Modified Example 2 of the First Embodiment

Modified Example 2 of the first embodiment illustrates an example of a vital sensor including a strain gauge that includes a resistor having a structure different from the structure of the resistor in the first embodiment. Note that, in Modified Example 2 of the first embodiment, description of the same components as in the above-described embodiment may be omitted.

Figure 7:
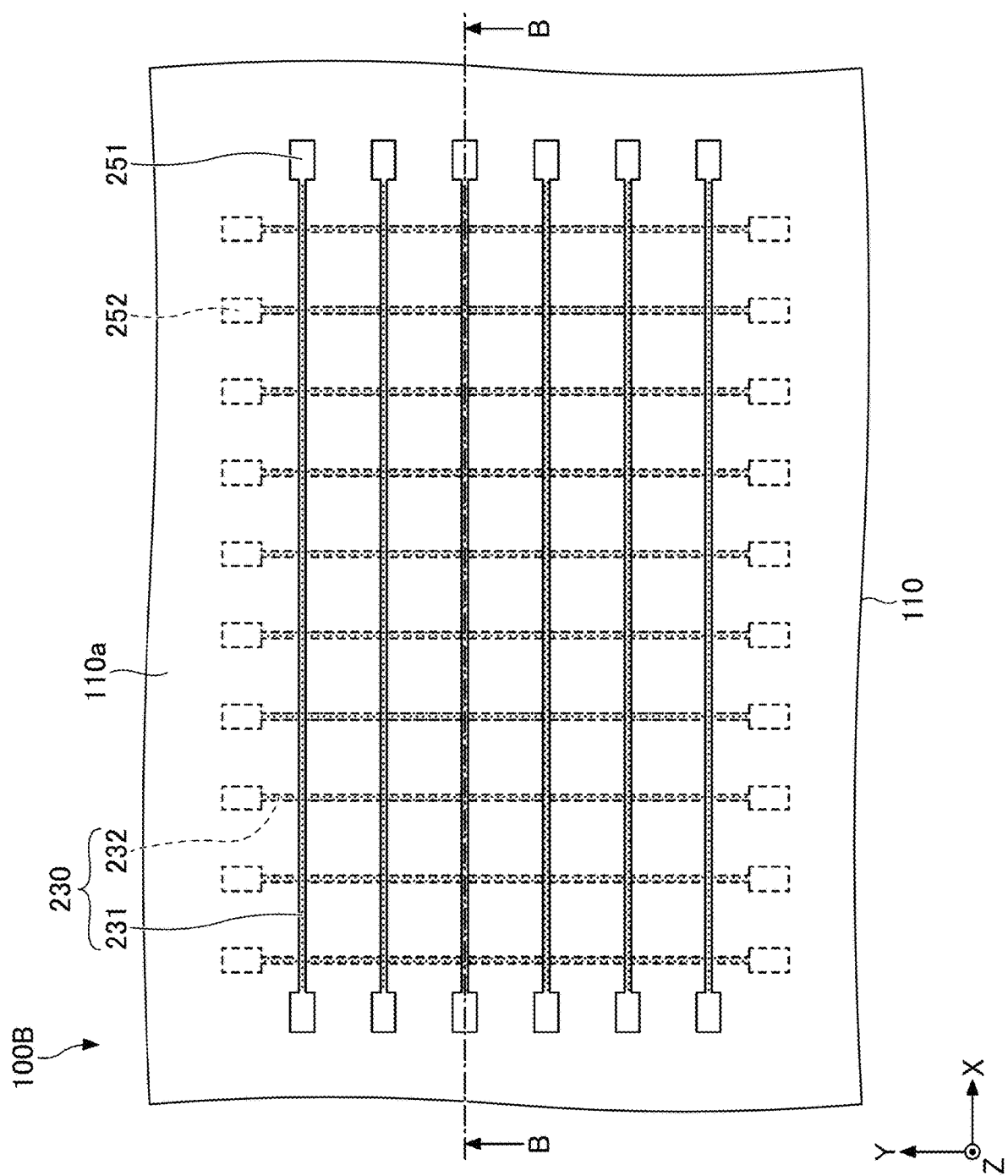
FIG. 7 is a plan view of one resistor, and the vicinity thereof, of a strain gauge according to Modified Example 2 of the first embodiment.
Figure 8:
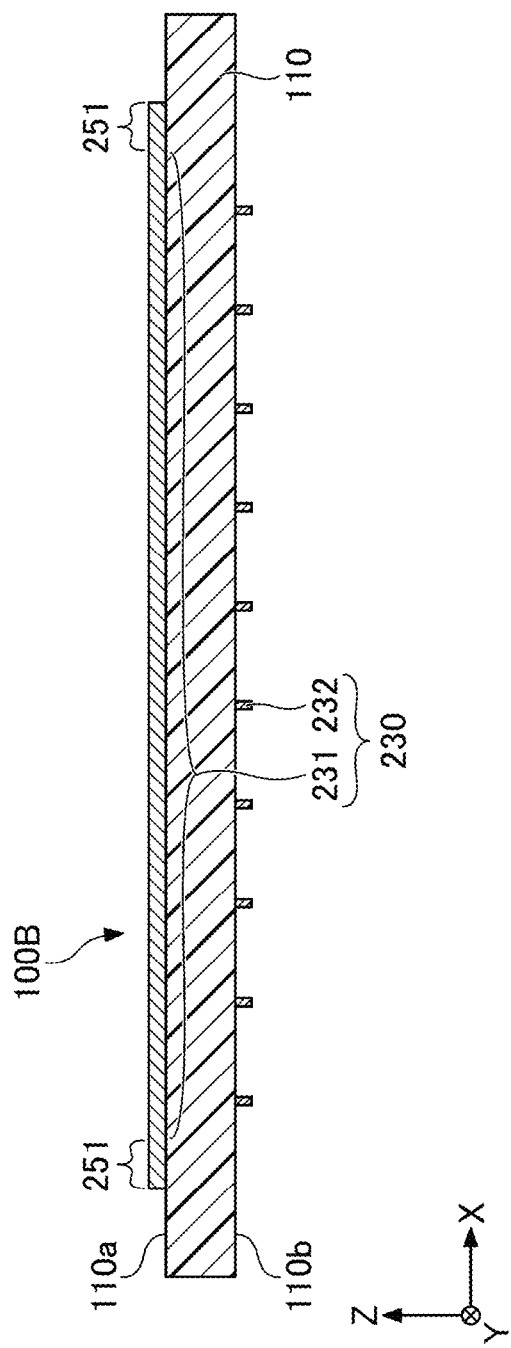
FIG. 8 is a cross-sectional view of one resistor, and the vicinity thereof, of the strain gauge according to Modified Example 2 of the first embodiment.

FIG. 7 is a plan view of one resistor, and the vicinity thereof, of the strain gauge according to Modified Example 2 of the first embodiment. FIG. 8 is a cross-sectional view of one resistor, and the vicinity thereof, of the strain gauge according to Modified Example 2 of the first embodiment, and illustrates a cross section thereof along line B-B in FIG. 7. As illustrated in FIG. 7 and FIG. 8, a strain gauge 100B includes a substrate 110, a resistor 230 (a plurality of resistive portions 231 and 232), and a plurality of electrodes 251 and 252.

The strain gauge 100B includes three sets each including the resistor 230 and the electrodes 251 and 252, and these sets are disposed on the single substrate 110. The resistors 230 in the sets each including the resistor 230 and the electrodes 251 and 252 are disposed at the same positions as the positions of the first resistor $130_1$, the second resistor $130_2$, and the third resistor $130_3$ of FIG. 1. However, three strain gauges each including, on the single substrate 110, one set including the resistor 230 and the electrodes 251 and 252 may be disposed on the strain generator 10.

The resistor 230 is formed on the substrate 110, and is a sensitive portion that continuously changes in resistivity in accordance with strain. The resistor 230 may be directly formed on the upper surface 110a and a lower surface 110b of the substrate 110, or may be formed via another layer at the upper surface 110a and the lower surface 110b of the substrate 110.

The resistor 230 includes the plurality of resistive portions 231 and 232 that are stacked via the substrate 110 that is an insulating layer. Note in FIG. 7 that, for the sake of convenience, the resistive portions 231 and 232 are illustrated with a mat pattern.

The plurality of resistive portions 231 form a thin film on the upper surface 110a of the substrate 110. In the thin film, the plurality of resistive portions 231 are juxtaposed in the Y direction at predetermined intervals, with longitudinal directions thereof being oriented in the X direction. The plurality of resistive portions 232 form a thin film on the lower surface 110b of the substrate 110. In the thin film, the plurality of resistive portions 232 are juxtaposed in the X direction at predetermined intervals, with longitudinal directions thereof being oriented in the Y direction. However, the plurality of resistive portions 231 and the plurality of resistive portions 232 do not necessarily orthogonally cross each other in a plan view thereof as long as they cross each other. For example, the resistor 230 is formed of a similar material to the material of the resistor 130.

No particular limitation is imposed on the width of the resistor 230, which may be appropriately selected in accordance with the intended purpose. However, for example, the width thereof can be from about 0.1 μm through about 1000 μm (1 mm). No particular limitation is imposed on the pitch of the resistors 230 next to each other, which may be appropriately selected in accordance with the intended purpose. However, for example, the pitch thereof can be from about 1 mm through about 100 mm. Note that, FIG. 7 and FIG. 8 illustrate six resistive portions 231 and ten resistive portions 232. The resistive portions 231 and 232 are provided in from about several hundreds through about several tens of thousands in practice.

The electrode 251 is extended from both ends of each of the resistive portions 231 in the upper surface 110a of the substrate 110, and in a plan view thereof, is formed into an approximately rectangular shape that is wider than the resistive portion 231. The electrode 251 is a pair of electrodes configured to output, to the exterior, change in resistivity of the resistive portion 231 caused by a compressive force. For example, a flexible substrate, a lead wire, or the like for external connection is bonded to the electrode 251. The upper surface of the electrode 251 may be covered with a metal having better solderability than the electrode 251. Note that, the resistive portion 231 and the electrode 251 are denoted by different reference numerals for the sake of convenience. However, these can be integrally formed of the same material in the same step.

The electrode 252 is extended from both ends of each of the resistive portions 232 in the lower surface 110b of the substrate 110, and in a plan view thereof, is formed into an approximately rectangular shape that is wider than the resistive portion 232. The electrode 252 is a pair of electrodes configured to output, to the exterior, change in resistivity of the resistive portion 232 caused by a compressive force. For example, a flexible substrate, a lead wire, or the like for external connection is bonded to the electrode 252. The upper surface of the electrode 252 may be covered with a metal having better solderability than the electrode 252. Note that, the resistive portion 232 and the electrode 252 are denoted by different reference numerals for the sake of convenience. However, these can be integrally formed of the same material in the same step.

Note that, by providing a penetrating interconnect (through-hole) that penetrates the substrate 110, the electrodes 251 and 252 may be integrated on the upper surface 110a side or the lower surface 110b side of the substrate 110.

The upper surface 110a of the substrate 110 may be provided with a cover layer (insulating resin layer) so as to cover the resistive portions 231 and expose the electrodes 251. Alternatively, the lower surface 110b of the substrate 110 may be provided with a cover layer (insulating resin layer) so as to cover the resistive portions 232 and expose the electrodes 252. By providing the cover layer, it is possible to prevent the resistive portions 231 and 232 from receiving mechanical damage and the like. Also, by providing the cover layer, it is possible to protect the resistive portions 231 and 232 from moisture and the like. Note that, the cover layer may be provided so as to cover the entire region excluding the electrodes 251 and 252.

When the resistive portion 231 and/or the resistive portion 232 in the strain gauge 100B is strained in receipt of the pressure attributed to the blood flow, the resistivity between a pair of electrodes connected to the strained resistive portion (the resistive portion 231 and/or the resistive portion 232) continuously changes in accordance with the magnitude of strain. Therefore, by monitoring the change in the resistivity detected from the electrodes 251 and 252, it is possible to know about the XY coordinate of a position at which the pressure attributed to the blood flow is detected, the intensity of the pressure, and changes therein.

Note that, the blood vessel is thin, and branches and changes in the blood flow as it is closer to the terminal. Therefore, there may be a case in which sufficient sensitivity is not obtained from resistors whose longitudinal directions are oriented in one direction. The resistor 230 having a lattice form, such as the strain gauge 100B, can provide information on pulse waves regardless of the branches of the blood vessel, the thickness of the blood vessel, and such states of the blood vessel as dilation and contraction, and thus can realize a vital sensor of higher accuracy.

Modified Example 3 of the First Embodiment

Modified Example 3 of the first embodiment illustrates another example of a vital sensor including a strain gauge that includes a resistor having a structure different from the structure of the resistor in the first embodiment. Note that, in Modified Example 3 of the first embodiment, description of the same components as in the above-described embodiment may be omitted.

Figure 9:
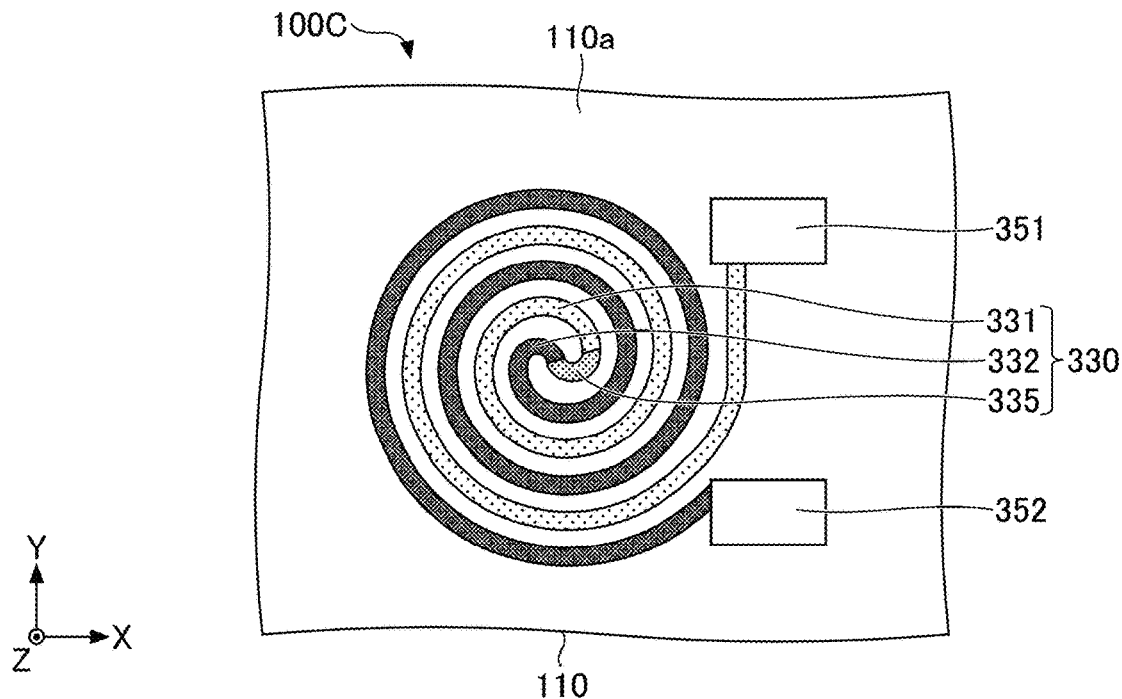
FIG. 9 is a plan view of one resistor, and the vicinity thereof, of a strain gauge according to Modified Example 3 of the first embodiment (part 1).

FIG. 9 is a plan view of one resistor, and the vicinity thereof, of a strain gauge according to Modified Example 3 of the first embodiment (part 1). As illustrated in FIG. 9, a strain gauge 100C includes the substrate 110, a resistor 330, and electrodes 351 and 352.

The strain gauge 100C includes three sets each including the resistor 330 and the electrodes 351 and 352, and these are disposed on the single substrate 110. The resistors 330 in the sets each including the resistor 330 and the electrodes 351 and 352 are disposed at the same positions as the positions of the first resistor $130_1$, the second resistor $130_2$, and the third resistor $130_3$ of FIG. 1. However, three strain gauges each including, on the single substrate 110, one set including the resistor 330 and the electrodes 351 and 352 may be disposed on the strain generator 10.

The resistor 330 is patterned in a circular swirl form in a plan view thereof. The resistor 330 is a single continuous pattern that connects the electrode 351 and the electrode 352 to each other. However, for the sake of convenience, a portion ranging from the electrode 351 to a return-back portion 335, where the pattern is returned back, is referred to as a first resistive interconnect 331, and a portion ranging from the return-back portion 335 to the electrode 352 is referred to as a second resistive interconnect 332. Note in FIG. 9 that, for the sake of convenience, the first resistive interconnect 331, the second resistive interconnect 332, and the return-back portion 335 are illustrated with mat patterns different from each other.

In the resistor 330, the first resistive interconnect 331 is extended from the electrode 351 and patterned clockwise from the outer periphery toward the center in the circular swirl form, thereby reaching the return-back portion 335. The second resistive interconnect 332 is extended from the return-back portion 335 and patterned counterclockwise from the center toward the outer periphery in the circular swirl form, thereby reaching the electrode 352.

The first resistive interconnect 331 and the second resistive interconnect 332 are, in principle, alternatingly disposed. That is, except for a portion near the return-back portion 335, what is next to the first resistive interconnect 331 is always the second resistive interconnect 332, and what is next to the first resistive interconnect 331 is always the second resistive interconnect 332. Except for the portion near the return-back portion 335, the first resistive interconnects 331 or the second resistive interconnects 332 are not next to each other. The resistor 330 is formed of, for example, a material similar to the material of the resistor 130.

When the strain generator 10 receives the blood pressure, a strain distribution of tension and compression concentrically occurs from the center of the strain generator 10. Therefore, by providing the resistor 330 in the circular swirl form so as to be along concentric circles, it is possible to detect strain at the entire circumference of the concentric circles, and efficiently detect strain that is slightly generated by the blood pressure.

Figure 10:
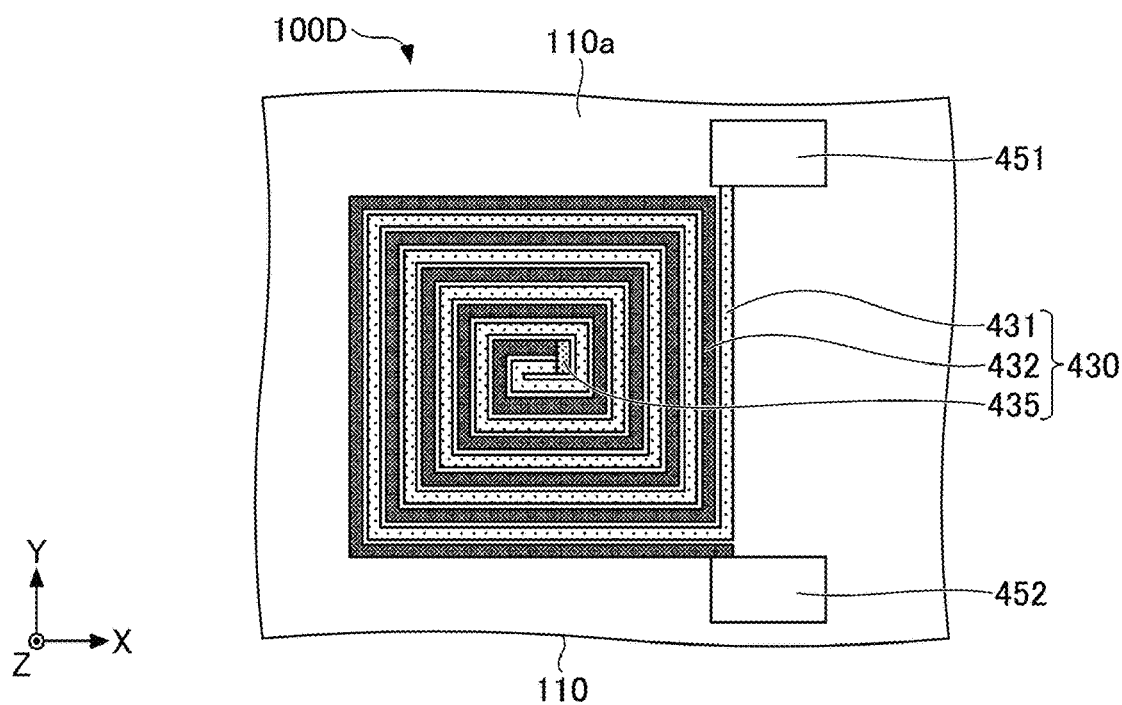
FIG. 10 is a plan view of one resistor, and the vicinity thereof, of the strain gauge according to Modified Example 3 of the first embodiment (part 2).

FIG. 10 is a plan view of one resistor, and the vicinity thereof, of the strain gauge according to Modified Example 3 of the first embodiment (part 2). As illustrated in FIG. 10, a strain gauge 100D includes the substrate 110, a resistor 430, and electrodes 451 and 452.

The strain gauge 100D includes three sets each including the resistor 430 and the electrodes 451 and 452, and these are disposed on the single substrate 110. The resistors 430 in the sets each including the resistor 430 and the electrodes 451 and 452 are disposed at the same positions as the positions of the first resistor $130_1$, the second resistor $130_2$, and the third resistor $130_3$ of FIG. 1. However, three strain gauges each including, on the single substrate 110, one set including the resistor 430 and the electrodes 451 and 452 may be disposed on the strain generator 10.

The resistor 430 is patterned in an angular swirl form in a plan view thereof. The resistor 430 corresponds to the resistor 330 except that the first resistive interconnect 331, the second resistive interconnect 332, and the return-back portion 335 are replaced with the first resistive interconnect 431, the second resistive interconnect 432, and the return-back portion 435. Also, the electrodes 351 and 352 are replaced with the electrodes 451 and 452.

In this way, the resistor is not limited to the circular swirl form, and may be the angular swirl form like the resistor 430. Alternatively, the resistor may be a swirl form other than the circular swirl form or the angular swirl form. In these cases, similar effects to the effects obtained in the case of disposing the resistor 330 in the circular swirl form are produced.

Figure 11:
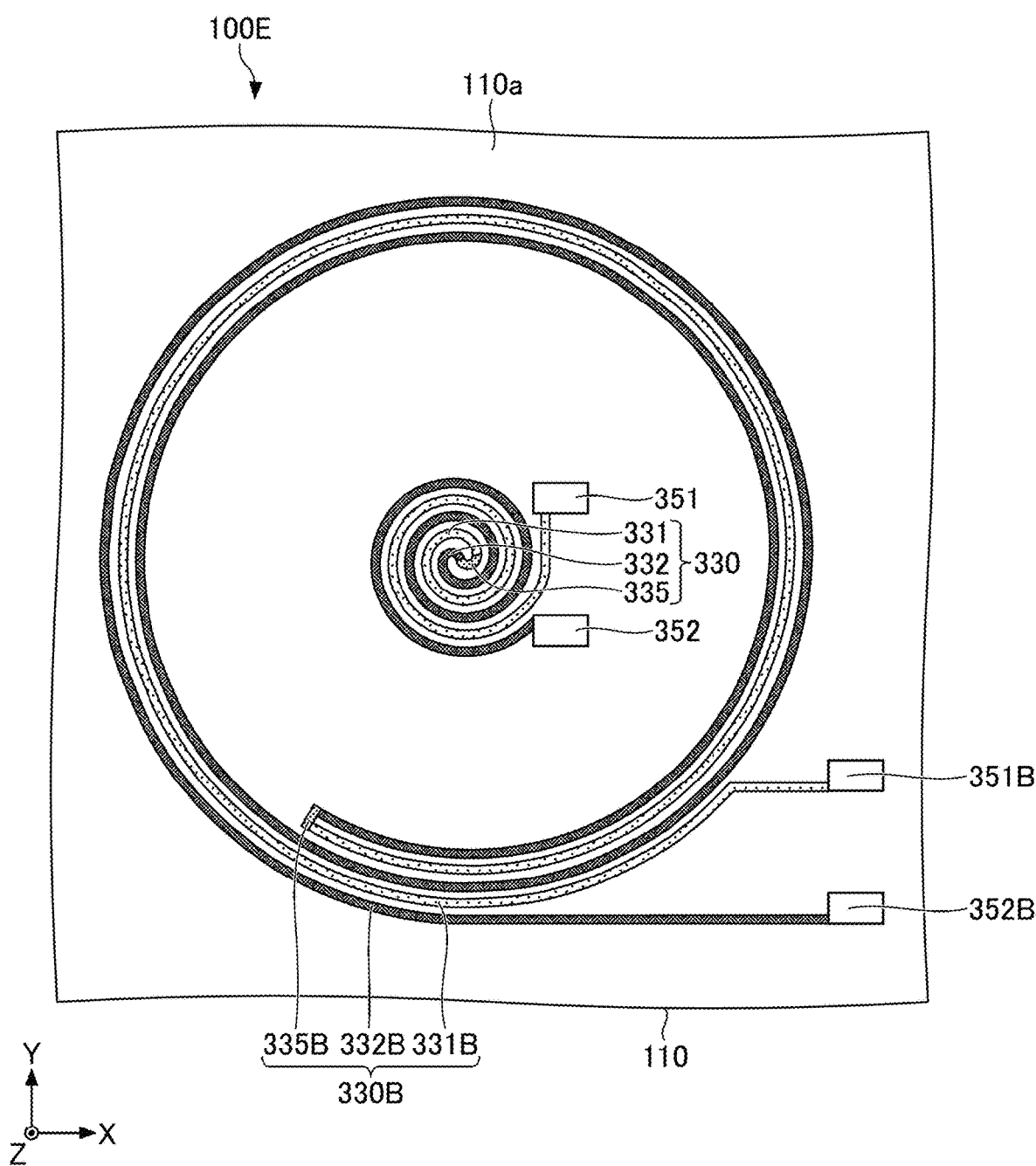
FIG. 11 is a plan view of one resistor, and the vicinity thereof, of the strain gauge according to Modified Example 3 of the first embodiment (part 3).

FIG. 11 is a plan view of one resistor, and the vicinity thereof, of the strain gauge according to Modified Example 3 of the first embodiment (part 3). As illustrated in FIG. 11, a strain gauge 100E is different from the strain gauge 100C in that a resistor 330B and electrodes 351B and 352B are added. The resistor 330B is, in a plan view thereof, a circular swirl pattern disposed outward of the resistor 330.

In the resistor 330B, the first resistive interconnect 331B is extended from the electrode 351B and patterned clockwise from the outer periphery toward the center in the circular swirl form, thereby reaching the return-back portion 335B. The second resistive interconnect 332B is extended from the return-back portion 335B and patterned counterclockwise from the center toward the outer periphery in the circular swirl form, thereby reaching the electrode 352B. The resistor 330 and the resistor 330B are disposed approximately concentrically.

The strain gauge 100E includes three sets each including the resistors 330 and 330B, the electrodes 351 and 352, and the electrodes 351B and 351B, and these are disposed on the single substrate 110. The resistors 330 and 330B in the sets each including the resistors 330 and 330B, the electrodes 351 and 352, and the electrodes 351B and 351B are disposed at the same positions as the positions of the first resistor $130_1$, the second resistor $130_2$, and the third resistor $130_3$ of FIG. 1. However, three strain gauges each including, on the single substrate 110, one set including the resistors 330 and 330B, the electrodes 351 and 352, and the electrodes 351B and 351B may be disposed on the strain generator 10.

In this way, the resistor may include the resistor 330 patterned in the circular swirl form, and the resistor 330B patterned in the other circular swirl form and disposed so as to enclose the resistor 330 in a plan view thereof. In this case, a half-bridge circuit can be formed with the resistor 330 and the resistor 330B. As a result, the output from the resistor can be doubled, and thus the blood flow can be detected with high accuracy. Note that, circular swirl-patterned resistors similar to the resistors 330 and 330B may also be disposed on the lower surface side of the strain generator 10. In this case, a full-bridge circuit can be formed therewith in combination with the resistors 330 and 330B on the upper surface side.

Figure 12:
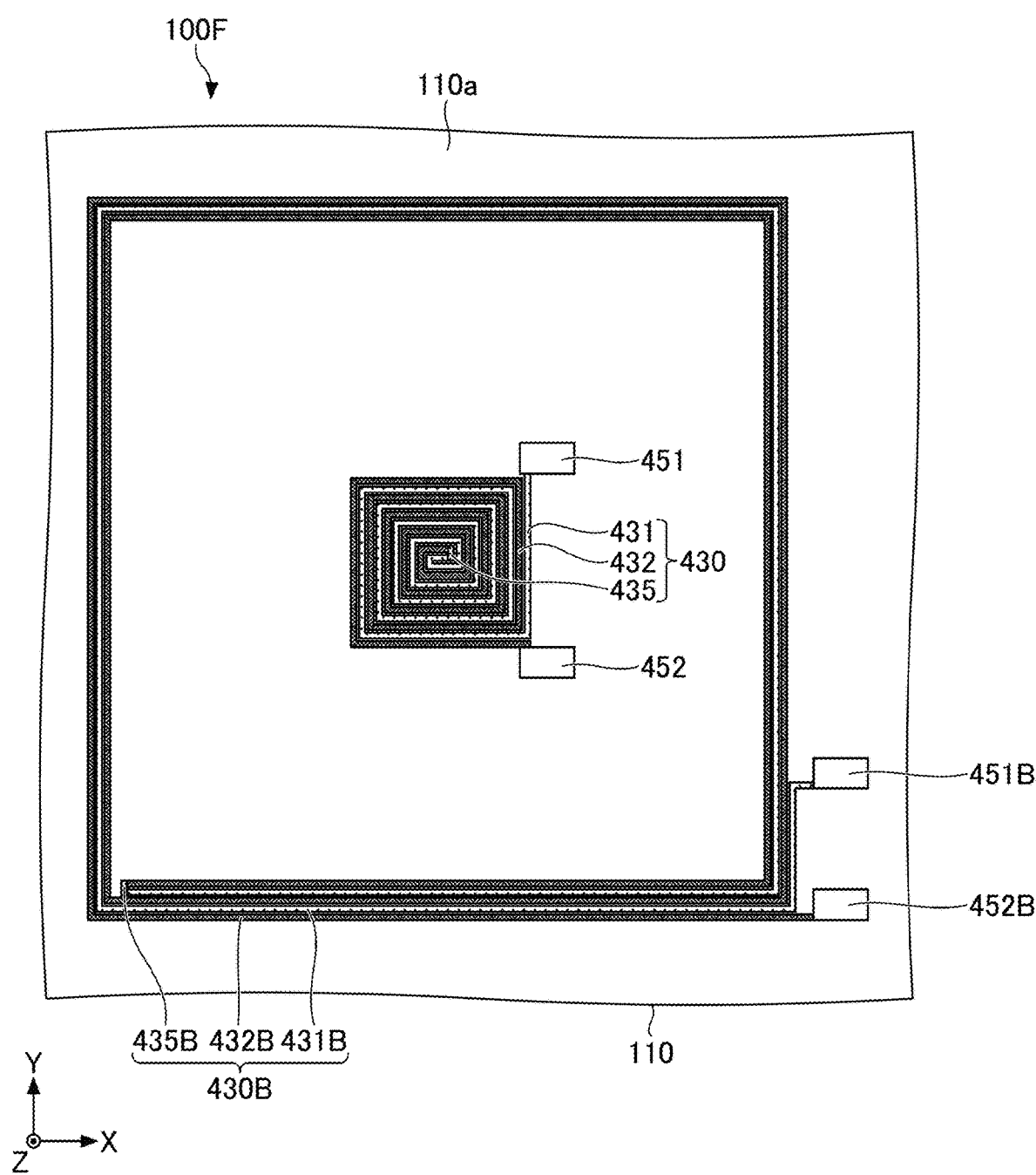
FIG. 12 is a plan view of one resistor, and the vicinity thereof, of the strain gauge according to Modified Example 3 of the first embodiment (part 4).

FIG. 12 is a plan view of one resistor, and the vicinity thereof, of the strain gauge according to Modified Example 3 of the first embodiment (part 4). As illustrated in FIG. 12, a strain gauge 100F is different from the strain gauge 100D in that a resistor 430B and electrodes 451B and 452B are added. The resistor 430B is, in a plan view thereof, an angular swirl pattern disposed outward of the resistor 430.

In the resistor 430B, a first resistive interconnect 431B is extended from the electrode 451B and patterned clockwise from the outer periphery toward the center in the angular swirl form, thereby reaching a return-back portion 435B. A second resistive interconnect 432B is extended from the return-back portion 435B and patterned counterclockwise from the center toward the outer periphery in the angular swirl form, thereby reaching the electrode 452B. The resistor 430 and the resistor 430B are disposed approximately concentrically.

In this way, angular swirl-patterned resistors 430 and 430B may be disposed in a bi-layered manner. In this case, similar effects to the effects obtained in the case of disposing the circular swirl-patterned resistors 330 and 330B in a bi-layered manner are produced. Note that, angular swirl-patterned resistors similar to the resistors 430 and 430B may also be disposed on the lower surface side of the strain generator 10. In this case, a full-bridge circuit can be formed therewith in combination with the resistors 430 and 430B on the upper surface side.

While preferable embodiments and the like have been described above in detail, the present invention is not limited to the above-described embodiments and the like, and various modifications and substitutions can be added to the above-described embodiments and the like without departing from the scope of claims as recited.

The present international application claims priority to U.S. Patent Application No. 63/193,162, filed on May 26, 2021 and Japanese Patent Application No. 2021-111065, filed on Jul. 2, 2021, and the contents of U.S. Patent Application No. 63/193,162 and Japanese Patent Application No. 2021-111065 are incorporated in the present international application by reference in their entirety.

REFERENCE SIGNS LIST 1, 1A vital sensor, 10 strain generator, 100, 100A, 100B, 100C, 100D, 100E, 100F strain gauge, 110 substrate, 110a upper surface, 110b lower surface, 130, 230, 330, 330B, 430, 430B resistor, $130_1$ first resistor, $130_2$ second resistor, $130_3$ third resistor, $130_4$ fourth resistor, $130_5$ fifth resistor, $130e_1$, $130e_2$ terminal, 140 interconnect, 141, 151 first metallic layer, 142, 152 second metallic layer, 150, 251, 252, 351, 351B, 352, 352B, 451, 451B, 452, 452B electrode, 160 cover layer, 231, 232 resistive portion, 331, 331B, 431, 431B first resistive interconnect, 332, 332B, 432, 432B second resistive interconnect, 335, 335B, 435, 435B return-back portion

The invention claimed is:

1. A vital sensor configured to monitor a blood flow, the vital sensor comprising:
   a strain generator configured to be attached to a measurement site in a subject; and
   a strain gauge disposed on the strain generator, wherein the strain gauge includes at least three resistors, each of the at least three resistors connected to an electrode via an interconnect, each of the at least three resistors having an elongated portion,
   with a first direction being a direction in which a blood vessel extends in the measurement site when the strain generator is attached to the measurement site and a second direction being a direction orthogonal to the first direction, longitudinal ends of the elongated portions of the at least three resistors are located in different positions in the first direction from each other, and the longitudinal ends of the elongated portions of the at least three resistors are located in different positions in the second direction from each other, each of the elongated portions of the at least three resistors has a multiple-folded pattern, and each of the at least three resistors includes a bent portion extending from the longitudinal end as a part of the multiple-folded pattern, the bent portion connecting the elongated portion to the interconnect.

2. The vital sensor according to claim 1, wherein the strain generator is attached to the measurement site so that the at least three resistors are at constant intervals with respect to the first direction and the second direction.

3. The vital sensor according to claim 1, wherein the at least three resistors include:
a first resistor;
a second resistor that is disposed at one side of the first resistor in the first direction and at one side of the first resistor in the second direction, when the strain generator is attached to the measurement site; and
a third resistor that is disposed at the other side of the first resistor in the first direction and at the other side of the first resistor in the second direction, when the strain generator is attached to the measurement site, and
the second resistor and the third resistor face each other via the first resistor.

4. The vital sensor according to claim 3, wherein the at least three resistors further include:
a fourth resistor that is disposed at the other side of the second resistor in the second direction, when the strain generator is attached to the measurement site; and
a fifth resistor that is disposed at the one side of the third resistor in the second direction, when the strain generator is attached to the measurement site, and
the fourth resistor and the fifth resistor face each other via the first resistor.

5. The vital sensor according to claim 1, wherein the at least three resistors include a first resistor, a second resistor, and a third resistor that are disposed with a grid direction thereof being oriented in a same direction,
positions of the first resistor, the second resistor, and the third resistor in the grid direction are different from each other, and the positions thereof in a direction orthogonal to the grid direction are different from each other, and
the second resistor and the third resistor face each other via the first resistor.

6. The vital sensor according to claim 5, wherein the at least three resistors further include a fourth resistor and a fifth resistor that are disposed with the grid direction thereof being oriented in the same direction,
a position of the fourth resistor in the grid direction is the same as a position of the second resistor in the grid direction, and is the same as a position of the third resistor in the direction orthogonal to the grid direction,
a position of the fifth resistor in the grid direction is the same as a position of the third resistor in the grid direction, and is the same as a position of the second resistor in the direction orthogonal to the grid direction, and
the fourth resistor and the fifth resistor face each other via the first resistor.

7. The vital sensor according to claim 5, wherein the strain generator is attached to the measurement site so that the first resistor, the second resistor, and the third resistor are disposed with the grid direction thereof being oriented in the first direction.

8. The vital sensor according to claim 1, wherein the resistors each include:
a plurality of first resistive portions that are juxtaposed with longitudinal directions thereof being oriented in the first direction, when the strain generator is attached to the measurement site; and
a plurality of second resistive portions that are juxtaposed with longitudinal directions thereof being oriented in the second direction, when the strain generator is attached to the measurement site, and
the first resistive portions and the second resistive portions are disposed via an insulating layer.

9. The vital sensor according to claim 1, wherein the resistors are formed of a film containing Cr, CrN, and $Cr_2N$.

10. The vital sensor according to claim 1, wherein a gauge factor is 10 or more.

11. The vital sensor according to claim 1, wherein CrN and $Cr_2N$ contained in the resistor are 20% by weight or less.

12. The vital sensor according to claim 11, wherein a percentage of the $Cr_2N$ in the CrN and the $Cr_2N$ is 80% by weight or more and less than 90% by weight.

13. The vital sensor according to claim 1, wherein two resistors of the at least three resistors are disposed such that the multiple-folded patterns of the two resistors are rotationally symmetrical to each other.

14. The vital sensor according to claim 1, wherein the at least three resistors include a first resistor, a second resistor, and a third resistor,
the longitudinal ends of the elongated portions of the first resistor and the second resistor are directed toward one side in the first direction, and
the longitudinal end of the elongated portion of the third resistor is directed toward another side in the first direction.

* * * * *